United States Patent [19]

Smith et al.

[11] 4,358,362
[45] Nov. 9, 1982

[54] METHOD FOR ENHANCING CATALYTIC ACTIVITY

[75] Inventors: Fritz A. Smith, Rye, N.Y.; Samuel A. Tabak, Wenonah, N.J.

[73] Assignee: Mobil Oil Corporation, New York, N.Y.

[21] Appl. No.: 225,293

[22] Filed: Jan. 15, 1981

[51] Int. Cl.$^3$ ............................................. C10G 53/08
[52] U.S. Cl. ..................................... 208/91; 208/291; 585/413; 585/448; 585/467
[58] Field of Search ............................ 208/89, 291, 91; 585/413, 448, 467

[56] References Cited

U.S. PATENT DOCUMENTS

| | | | |
|---|---|---|---|
| 2,925,375 | 2/1960 | Fleck et al. | 208/89 |
| 3,189,539 | 6/1965 | Sieg | 208/254 R |
| 3,732,326 | 5/1973 | Chen | 208/820 |
| 3,767,563 | 10/1973 | Woodle | 208/85 |
| 3,894,938 | 7/1975 | Gorring et al. | 208/97 |
| 3,989,617 | 11/1976 | Yan | 208/87 |
| 4,028,223 | 6/1977 | Hayes et al. | 208/91 |
| 4,137,154 | 1/1979 | Audeh | 208/254 |
| 4,222,855 | 9/1980 | Pelrine | 208/111 |
| 4,229,282 | 10/1980 | Peters et al. | 208/111 |

Primary Examiner—Delbert E. Gantz
Assistant Examiner—G. E. Schmitkons
Attorney, Agent, or Firm—Charles A. Huggett; Michael G. Gilman; Laurence P. Hobbes

[57] ABSTRACT

A hydrocarbon feed for use in a catalytic conversion process that utilizes a zeolite catalyst, and that contains a catalytically deleterious impurity, is refined by contact with a zeolitic sorbent. The invention is applicable to dewaxing, with an example illustrating reduction by 100° F. of the initial equilibrium (lineout) temperature by the method of this invention. Other reactions include conversions of aromatic hydrocarbons such as alkylation, isomerization and disproportionation.

18 Claims, 1 Drawing Figure

METHOD FOR ENHANCING CATALYTIC ACTIVITY

BACKGROUND OF THE INVENTION

1. Field of the Invention

This invention is concerned with processes that employ crystalline molecular sieve zeolites as catalysts. It is particularly concerned with processes that use a fixed bed of catalyst to convert an appropriate feed to desired products, and with pretreatment of the feed to make it more readily converted by the catalyst. This invention is advantageous for the catalytic dewaxing of petroleum fuels and lubricants.

2. Prior Art

Modern petroleum refining is heavily dependent on catalytic processes which chemically change the naturally occurring constituents of petroleum. Such processes include hydrocracking, catalytic cracking, reforming and hydrotreating. Historically, the processes all depended on the discovery that chemical change could be induced by contacting a suitable petroleum fraction with a suitable porous inorganic solid at elevated temperature. If hydrogen under pressure is essential to the desired conversion, such as in hydrocracking, a hydrogenation metal is included with the porous catalyst to make the hydrogen effective.

The porous inorganic solids that were originally found useful for catalytic processes included certain clays, aluminas, silica-aluminas and other silicas coprecipitated with magnesia, for example, and such solids are still extensively used in the industry. In general, all of these solids had pores that were not of uniform size, and most of the pore volume was in pores having diameters larger than about 30 Angstroms, with some of the pores as large or larger than 100 Angstroms. As will become evident from the paragraphs which follow, a large fraction of the molecules present in a hydrocarbon feed, such as a gas oil, is capable of entering the pores of the typical porous solids described above.

In recent years much attention has been given to the synthesis and properties of a class of porous solids known as "molecular sieves." These are porous crystalline solids usually composed of silica and alumina, and, because the pore structure is defined by the crystal lattice, the pores of any particular molecular sieve have a uniquely determined, uniform pore diameter. The pores of these crystals are further distinguished from those in the earlier used solids by being smaller, i.e., by having effective pore diameters not greater than about 13 Angstroms. These solids, when dehydrated, act as sorbents that discriminate among molecules of different shape, and for that reason were first called "molecular sieves" by J. W. McBain. The term "effective pore diameter" as used herein means the diameter of the most constricted part of the channels of the dehydrated crystal as estimated from the diameter of the largest molecule that the crystal is capable of sorbing. Zeolite molecular sieves are available that have effective pore diameters ranging from about 3 Angstroms, which is too small to allow occlusion of any hydrocabon in the pores, to about 13 Angstroms, which allows occlusion of molecules as large as 1,3,5-triethylbenzene. The structures and uses of these solids are described in "Zeolite Molecular Sieves," by Donald W. Breck, John Wiley and Sons, New York (1974), the entire content of which is incorporated herein by reference for background purposes. As indicated by Breck, the zeolite molecular sieves are useful as adsorbents (ibid, page 3), and in catalysts (ibid, page 2).

In spite of the small pores which are characteristic of zeolite molecular sieves, certain of these materials have been found to be highly effective as hydrocarbon conversion catalysts. The conversion of gas oil to gasoline and distillate by catalytic cracking, the alkylation of benzene to ethylbenzene, the isomerization of xylenes and the disproportionation of toluene all involve molecules which are smaller in critical diameter than 1,3,5-triethylbenzene, and such molecules are occluded and acted upon by zeolite molecular sieves having an effective pore diameter of about 10 Angstroms. A particularly interesting catalytic transformation which requires a molecular sieve catalyst is the reduction of the pour point of waxy distillates and residual hydrocarbon fractions. Effective pour point reduction depends on the selective conversion of normal, high melting point paraffin molecules that have an effective critical diameter of about 5 Angstroms to substances of lower molecular weight that are easily separated from the low-pour product. Effective catalytic dewaxing depends at least in part on the regularity of the pore size of the crystalline zeolites, which allows selective conversion of unwanted constituents.

The developments briefly described above are only indicative of the commercial importance of the molecular sieve zeolites and of the academic interest in these materials, which is more accurately reflected by the thousands of patents and publications on the subject. By far the major part of this importance stems from the catalytic properties that may be found in appropriate circumstances within the relatively small pores, together with the regularity in the shape of the pores which permits the molecular sieve catalyst to act selectively on molecules having a particular shape. This latter phenomenon has come to be known as "shape-selective catalysis." A review of the state of the catalytic art is found in "Zeolite Chemistry and Catalysis" by Jule A. Rabo, ACS Monograph 171, American Chemical Society, Washington, D.C. (1976), the entire content of which is herein incorporated by reference for background purposes. See particularly Chapter 12 titled "Shape Selective Catalysis."

The dewaxing of oils by shape selective cracking and hydrocracking over zeolites of the ZSM-5 type is discussed and claimed in U.S. Pat. No. Re 28,398 to Chen et al. U.S. Pat. No. 3,956,102 discloses a particular method for dewaxing a petroleum distillate with a ZSM-5 type catalyst. Typical aging curves are shown in sheet 2 of the drawing of the U.S. Pat. No. 3,956,102. U.S. Pat. No. 3,894,938 to Gorring et al. discloses that the cycle life of a ZSM-5 dewaxing catalyst is longer with a virgin feed stream than it is with the same feedstream after it has been hydrotreated. Catalytic dewaxing of petroleum stocks in which a mordenite type of molecular sieve catalyst is used is described in the Oil and Gas Journal, Jan. 6, 1975 issue at pages 69–73. See also U.S. Pat. No. 3,668,113. All of the foregoing patents and the literature reference are herein incorporated by reference.

BRIEF SUMMARY OF THE INVENTION

It has now been found that in general a dewaxing process in which a zeolite molecular sieve dewaxing catalyst is used becomes more effective when the feed, prior to dewaxing, is contacted under sorption conditions, as more fully described hereinbelow, with a zeolite molecular sieve having an effective pore diameter at least as large as the dewaxing catalyst. The terms "more effective" as used herein means that the dewaxing catalyst behaves as if it were catalytically more active or more resistant to aging when the feed stream is pretreated as disclosed. Thus, the refiner, when using the improved method of this invention to reduce the pour point of a waxy feed to some predetermined temperature, may elect to take advantage of the increased catalyst activity by reducing the inventory of dewaxing catalyst; or, by reducing the operating temperature of the zeolite dewaxing catalyst from the temperature required by the prior art; or, he may elect to increase the space velocity of the feed and obtain more product with the same pour point reduction as was obtained by the prior art method; or, he may extend the cycle life of the dewaxing catalyst by running the process with a lower initial equilibrium temperature and finishing with the same end of cycle temperature as in the prior art.

It is not known precisely why pretreating the feed with a zeolite molecular sieve maintained under sorption conditions serves to increase the effectiveness of the dewaxing catalyst. While not wishing to be bound by theory, it may be postulated that the feed contains minute amounts of catalytically deleterious impurities which, in the prior art, were sorbed by the catalyst and served as catalyst poisons. It is further speculated that the content of these poisons is reduced by the pretreatment method of this invention with the effect that the catalytic activity of the dewaxing catalyst appears to be increased, or, that the reactivity of the feed has been increased. It seems appropriate to consider the pretreatment described herein as a method for refining the feed, and that term will be used herein in the context and spirit of this paragraph. The precise nature or composition of the catalyst poisons is not known, but again one may speculate that basic nitrogen compounds, and oxygen and sulfur compounds, may be involved.

It should be noted that the zeolite molecular sieve sorbent, as will be illustrated further below, is unusually effective in increasing the apparent activity of the dewaxing catalyst. Substitution of a clay or other sorbent for the zeolite also may produce some increase, but of much lesser magnitude, even though the clay may remove a greater fraction of nitrogen compounds than is removed by the zeolite. And, although it may prove useful in some instances to measure basic nitrogen level, for example, as an index for degree of refinement of the feed, an example later presented herein suggests that such a measurement by itself may be misleading.

In brief, it is conceivable that the zeolite sorbent selectively removes and effectively retains those poisons that have a shape sufficiently small to enter the catalyst pores, leaving only the larger poisons available for contact with the catalyst. Since these can act only on non-selective surface sites, they may in some cases serve to increase the shape selectively of the dewaxing catalyst, or at worst to do little harm.

Contemplated as within the scope of this invention is to regenerate the zeolite molecular sieve sorbent at intervals, as needed.

BRIEF DESCRIPTION OF THE DRAWING

The FIGURE illustrates one embodiment of the dewaxing process of this invention.

SPECIFIC EMBODIMENTS

Figure 1:
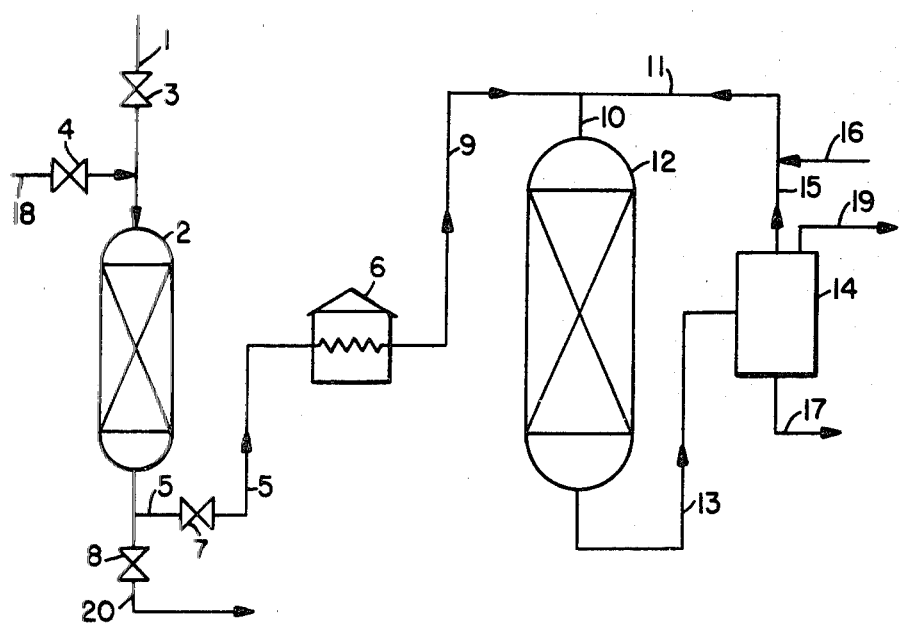

The feed to be dewaxed by the process of this invention may be any waxy hydrocarbon oil that has a pour point which is undesirably high. Petroleum distillates such as atmospheric tower gas oils, kerosenes, jet fuels, vacuum gas oils, whole crudes, reduced crudes and propane deasphalted residual oils are contemplated as suitable feeds. Also contemplated are oils derived from tar sands, shale, and coal. For purposes of this invention, all of the above described feeds may be considered suitable and all of these feeds are expected to benefit when dewaxed by the method of this invention.

The first step of the process of this invention requires that the feed be treated by contact with a sorbent under sorption conditions effective to remove at least some of the deleterious impurity. These conditions may cover a fairly wide range of time, temperature and pressure, and may be conducted in the absence or presence of hydrogen. The conditions, both broad and preferred, for this step of the process are indicated in Table I.

The catalytically deleterious impurities, or poisons, will be referred to herein as "contaminants" regardless of whether these occur naturally associated with the feed or are acquired by the feed from some known or unknown source during transportation, processing, etc.

TABLE I

| | SORPTION CONDITIONS | |
|---|---|---|
| | Broad | Preferred |
| Temperature, °F. | 35–350 | 65–200 |
| Pressure, psig | 0–3000 | 25–1500 |
| LHSV, hr$^{-1}$ | 0.1–100 | 0.2–20 |

In general, although it is preferred to conduct the treating step in a flow system, wherein the sorbent particles are in the form of a fixed bed of 1/16 inch to ¼ inch extrudate or pellets, other modes of contact may be employed such as slurrying the feed oil with a finely powdered sorbent followed by centrifugation and recycle of the sorbent. The precise conditions selected for the sorption step will be determined by various considerations, including the nature of the feed and the desired degree of refinement, the latter being judged from the observed catalytic consequences of the treatment.

For purposes of this invention, the sorbent consists of a molecular sieve zeolite having pores with an effective diameter of at least about 5 Angstroms. Illustrative of zeolites with pores of 5 Angstroms are zeolite A in the calcium salt form, chabazite and erionite, which sorb normal paraffins but exclude all other molecules of larger critical diameter. Other zeolites which may be used which have larger pore diameters include zeolite X, zeolite Y, offretite and mordenite. The last group of zeolites sorb molecules having critical diameters up to about 13 Angstroms, and all of them sorb cyclohexane freely.

In addition to the zeolites already enumerated, any of the zeolites described more fully hereinbelow which are useful as dewaxing catalysts also may be used as sorbents. In fact, in a preferred embodiment of this invention, the zeolite utilized as sorbent and as dewaxing catalyst have the same crystal structure. Since the dewaxing catalyst will be more fully described hereinbelow, it is unnecessary at this point to repeat the description.

In general, the pretreated feed is separated from the sorbent and passed to the catalytic dewaxing step where its pour point is reduced, usually by selective conversion of the high molecular weight waxes to more volatile hydrocarbon fragments.

Various embodiments of the present invention are contemplated. In one of these, the feed is contacted with a dewaxing catalyst under sorption conditions, after which a pretreated feed is recovered and passed to storage. The material used as sorbent is now treated, for example with steam at elevated temperature, to remove the sorbed deleterious impurity, and the stored treated hydrocarbon is passed over the regenerated sorbent now maintained at dewaxing conditions. In general, however, it is more effective to employ at least one separate bed of molecular sieve zeolite as sorbent, as will now be illustrated by reference to the FIGURE of the drawing.

The drawing illustrates one embodiment of the present invention. A hydrocarbon oil feed, such as a gas oil with a pour point of 75° F., is passed via line 1 to sorption tower 2 which is filled with a molecular sieve zeolite such as ZSM-5 containing a small amount of nickel. Valve 3 is of course open in this stage of the operation, and valve 4 is maintained closed. The treated oil passes out of sorption tower 2 via line 5 and is heated to dewaxing temperature in furnace 6. Valve 7 is maintained open during this phase of the operation and valve 8 is maintained closed. The heated oil is passed from the furnace via lines 9 and 10 along with hydrogen introduced via line 11 to the catalytic dewaxing reactor 12 filled with ZSM-5 dewaxing catalyst that contains a small amount of nickel. The dewaxed oil and cracked fragments together with excess hydrogen are passed from the dewaxing reactor 12 via line 13 to high pressure separator 14. The excess hydrogen passes from high pressure separator 14 via lines 15 and 11 and is recycled to the dewaxing reactor. Fresh make-up hydrogen is added via line 16. A bleed stream of gas is removed via line 19. The dewaxed oil and light ends are removed from the high pressure separator via line 17 and are passed to downstream facilities for recovering a dewaxed oil having a pour point of 20° F., for example, and the separated light fraction.

After a certain period of operation, the sorbent contained in vessel 2 becomes ineffective and needs to be regenerated. This may be done by shutting valves 3 and 7 and introducing stripping steam via line 18 and valve 4 into vessel 1 and removing the excess steam and deleterious impurities via valve 8 and line 20. Various stripping gases may be used in place of steam such as heated air, nitrogen or hydrogen gas. The sorbent also may be regenerated by burning in air at elevated temperature. The preferred method of regeneration are to use steam at about 350° F. or hydrogen gas at about 900° F.

It will of course be evident to one skilled in the art that instead of the single sorption tower shown in FIG. 1, two such towers may be used such that one of them is being regenerated while the other is on stream to permit continuous rather than intermittant dewaxing.

The step of catalytically dewaxing the pretreated feed is illustrated for different hydrocarbon oils in U.S. Pat. No. Re 28,398 and in U.S. Pat. No. 3,956,102 and in U.S. Pat. No. 4,137,148, for example. The entire content of these patents are herein incorporated by reference. It will be understood that the reaction conditions will be milder, in general, when adapting the dewaxing step to the pretreated feed as described herein. The dewaxing step may be conducted with or without hydrogen, although use of hydrogen is preferred. It is contemplated to conduct the dewaxing step at the dewaxing conditions shown in Table II.

TABLE II

| | DEWAXING STEP | |
|---|---|---|
| | Broad | Preferred |
| | | Without Hydrogen |
| Temperature, °F. | 400–1000 | 500–800 |
| LHSV, hr$^{-1}$ | 0.3–20 | 0.5–10 |
| Pressure, psig | 0–3000 | 25 to 1500 |
| | | With Hydrogen |
| Temperature, °F. | 400–1000 | 500–800 |
| LHSV, hr$^{-1}$ | 0.1–10 | 0.5–4.0 |
| H$_2$/HC mol ratio | 1–20 | 2–10 |
| Pressure, psig | 0–3000 | 200–1500 |

A particularly preferred embodiment of the dewaxing process of this invention is provided when the molecular sieve zeolite of the dewaxing catalyst is selected from a member of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred to use zeolites having higher ratios than about 30. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also included within this definition are substantially pure silica analogs of the useful zeolites described herein, that is to say those zeolites having no measurable amount of aluminum (silica to alumina mole ratio of infinity) but which otherwise embody the chracteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory generally would not offer sufficient constraint to produce advantageous conversions, it is noted that the puckered 12-ring structure of TMA offretite does show some constrained access. Other 12-ring structures may exist which may be operative for other reasons such as the presence of cations which may restrict the pore diameter. Therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials.

ZSM-5 is described in greater detail in U.S. Pat. Nos. 3,702,886 and Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 is more particularly described in U.S. patent application Ser. No. 56,754 filed July 12, 1979 and in, a continuation of Ser No. 064,703 filed on or about Nov. 18, 1980.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 and ZSM-11 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

Certain aspects of the present invention will now be illustrated by reference to examples which are not to be construed as limiting the scope of this invention, which scope is determined by this entire specification including the claims thereof.

EXAMPLES

EXAMPLE 1

A Nigerian gas oil having a nominal boiling range of 625°–775° F. was taken as one example of a contaminated feed. The raw gas oil had the properties shown in Table III.

TABLE III

| Raw Nigerian Gas Oil | |
|---|---|
| °API | 29.2 |
| Pour Point, °F. | 75 |
| Wt % S (Sulfur) | 0.18 |
| Wt % N (Nitrogen) | 0.03 |
| ppm Basic N | 262 |

Portions of the raw gas oil were mixed with varying amounts of crystalline zeolite ZSM-5 that had been incorporated in a matrix and extruded to form 1/16 inch extrudate that contained about 65 wt.% zeolite. The particular ZSM-5 used as sorbent was H-ZSM-5 with a $SiO_2/Al_2O_3$ ratio of 70:1 and an "alpha" value of 175. The dried, calcined extrudate had the properties shown in Table IV. After the mixtures of oil and extrudate had been allowed to stand overnight at 200° F., the oil was decanted and analyzed with the results shown in Table V.

TABLE IV

| ZSM-5 Extrudate | |
|---|---|
| Density, GM/CC | |
| Packed | .59 |
| Particle | .89 |
| Real | 2.66 |
| Surface Area, $M^2/GM$ | 365. |
| Pore Vol., CC/GM | .748 |
| Ave. Pore Dia., A | 92. |

TABLE V

| ZSM-5 Refining of Nigerian Gas Oil | | | |
|---|---|---|---|
| Extrudate/Oil (Wt/Wt) | PPM Basic N | Wt % N | Wt % S |
| 0 | 262 | .0340 | 0.18 |
| .034 | 235 | .0300 | 0.17 |
| .068 | 192 | .0260 | 0.16 |
| .136 | 166 | .0230 | 0.14 |

Example 1 illustrates the method of this invention for refining a waxy hydrocarbon oil feed. The permitted contact time was dictated by convenience, it being indicated by other experiments that equivalent results would be obtained with about one hour contact.

EXAMPLE 2

A ZSM-5 extrudate was placed in a fixed-bed catalytic reactor. The particular ZSM-5 used as catalyst had been activated by calcination, and had a silica to alumina ratio of about 160, an "alpha" activity of 114, and contained 0.54 wt.% nickel and about 0.02 wt.% sodium. The raw gas oil having the properties shown in Table III and hydrogen were passed over the catalyst under dewaxing conditions, in this instance at 400 psig, 1 LHSV with a hydrogen circulation rate of 2500 SCF/Bbl. The temperature was adjusted periodically to give a 330° F. product having a pour point of about 0° F. The temperature required for the first seventeen days of operation are given in Table VI.

TABLE VI

| Days on Stream | Operating Temperature, °F. |
|---|---|
| 1 | 565 |
| 3 | 635 |
| 5 | 685 |
| 8 | 725 |
| 11 | 750 |
| 14 | 752 |
| 16 | 754 |
| 17 | 755 |

Example 2 illustrates a typical prior art dewaxing run. It will be noted that a relatively rapid increase in temperature is required for about the first eleven days to maintain product quality, after which a relatively steady temperature may be maintained, in this instance at about 750° F. The temperature at which this steady operation sets in is referred to herein as the "initial equilibrium temperature." It will be recognized that this temperature may slowly increase with catalyst age until some prescribed limit is reached, necessitating regeneration of the catalyst. In any case, the initial equilibrium temperature is determined predominantly by the nature of the feed, all else being equal. The equilibrium temperature observed after the initial equilibrium temperature is equal to it or higher in normal, steady operation.

EXAMPLE 3

A batch of refined Nigerian gas oil was prepared from the raw gas oil described in Table III by the method described in Example 1 except that a sorbent to oil weight ratio of 0.071 was used and the oil was treated for 16 hours at 200° F. The refined oil had 215 ppm basic nitrogen.

The prior art catalytic dewaxing run described in Example 2 was terminated at 17 days by switching from the raw gas oil feed to the above-described refined feed, without changing the catalyst.

The temperature required to maintain a 0° F. pour point 330° F.+ product was observed to decrease over the next four days to 655° F., with an indication that a new initial equilibrium temperature would set in at about 650° F. or lower.

This example illustrates one embodiment of the dewaxing process of the present invention wherein a refined feed, although still containing a substantial amount of basic nitrogen, is dewaxed at an equilibrium temperature substantially below that required for the raw feed.

EXAMPLE 4

This example is provided to show the effect of pretreatment of the raw gas oil with a clay sorbent compared with refining according to the present invention. A commercial clay sorbent known as "Attagel 40" was prepared as extridate with the properties shown in Table VII.

TABLE VII

| Density, GM/CC | |
|---|---|
| Packed | .47 |
| Particle | .82 |
| Real | 2.55 |
| Surface Area, M$^2$/GM | 139. |
| Pore Vol., CC/GM | .828 |
| Ave. Pore Dia., A | 238. |

A portion of the raw gas oil described in Table III was treated in the same manner as described in Example 3 except that the clay sorbent was substituted for the crystalline zeolite sorbent. The treated oil was found to have a basic nitrogen content of 230 ppm.

EXAMPLE 5

The catalytic dewaxing run described in Example 3 was terminated after the catalyst had been on stream for a total of 21 days, by switching from the refined gas oil feed to the pretreated feed of Example 4, without changing the catalyst.

The temperature required to maintain 0° F. pour point product was observed to increase from about 665° F. to about 755° F. over four days of operation, at which point the run was terminated.

Example 5 illustrates that removal of basic nitrogen does not necessarily provide a feed which is more readily dewaxed. Thus, for purposes of the present invention, the terms "refine" and "refined," as used herein, refer to treatment with a crystalline zeolite sorbent as described herein and to a product that evidences a demonstrable catalytic advantage, such as a reduced initial equilibrium temperature, an increased rate of conversion, or the like.

EXAMPLE 6

This examples illustrates the process of this invention applied to a hydrotreated Occidental Shale Oil. The raw feed had the properties shown in Table VIII.

TABLE VIII

| Properties of Hydrotreated Shale Oil | |
|---|---|
| °API | 36.11 |
| Basic N, ppm | 340 |
| Pour Point | 55° F. |
| B.P., °F. | |
| IBP/5% | 153/295 |
| 20/50% | 441/581 |
| 70/95% | 690/905 |
| E.P. | 1027 |

The oil was refined by contacting 5 parts by weight of oil with 1 part by weight of ZSM-5 extrudate as sorbent. The ZSM-5 content of the extrudate was about 65 wt.%, the balance being an alumina matrix, and the ZSM-5 had a SiO$_2$/Al$_2$O$_3$ ratio of 70. The refined oil contained less than 5 ppm of basic nitrogen.

Both the untreated oil and the oil refined as described were dewaxed at 0° F. pour point for the 380° F.+ fraction and the initial equilibrium temperature was determined in each case. The dewaxing conditions were the same as those described in Example 2, and the catalyst was similar to that used in the Example except that it had a slightly lower "alpha" value of 101.

The initial equilibrium temperature determined for the raw oil was 775° F. The refined oil treated under the same conditions gave an initial equilibrium temperature of 650° F., i.e., 125° F. lower than for the raw oil.

CONTEMPLATED EQUIVALENTS

The process of this invention has been described up to this point in terms of catalytic dewaxing. However, as will be recognized by one skilled in the catalytic art, the advantages afforded by this invention equally well apply to any hydrocarbon conversion process in which a crystalline zeolite catalyst is used and in which the feed contains a catalytically deleterious impurity.

Thus, contemplated as within the scope of this invention, is to refine a hydrocarbon feed prior to catalytic conversion at a temperature of 400° to 1000° F. with a catalyst comprising a crystalline zeolite having a constraint index of 1 to 12, and a dried crystal density in the hydrogen form of not less than 1.6 grams per cubic centimeter. Such feeds include not only waxy hydrocarbon oils characterized by a pour point undesirably high for the particular use intended, but also various aromatic hydrocarbons such as toluene, xylenes, benzene, and mixtures thereof. The catalytic conversions contemplated include: the isomerization of xylenes for the purpose of manufacturing para-xylene; the disproportionation of toluene to form xylenes and benzene; the alkylation of benzene and toluene with methanol to add methyl groups to the benzene ring; and the alkylation of aromatic hydrocarbons such as benzene and toluene with ethylene to form ethylbenzene and para-ethyltoluene, respectively. Also contemplated as within the scope of this invention is to refine an aromatic hydrocarbon feed and to subject the refined feed to a catalytic conversion such as isomerization, disproportionation, or alkylation with methanol or with ethylene, and to refine a waxy hydrocarbon oil and to subsequently catalytically dewax the refined oil. For purposes of the present invention, the preferred crystalline zeolites are ZSM-5, ZSM-11, intergrowths of ZSM-5 and ZSM-11, ZSM-12, ZSM-23, ZSM-35, ZSM-38, and ZSM-48. As is known to those skilled in the art, any of these zeolites may be recognized from its x-ray diffraction pattern which results essentially from its crystal structure, the alumina and cation content of the crystal having but little effect on the pattern. Thus, as illustrated previously, the crystalline zeolite used to refine the feed and that used as catalyst may have the same crystal structure and either the same or a different chemical compositions. Also within the scope of this invention is to refine the feed with a crystalline zeolite having a crystal structure different from that of the zeolite used in the catalyst. For purposes of this invention, the preferred crystalline zeolites are ZSM-5, ZSM-11 and intergrowths thereof.

In order for a hydrocarbon feed to be suitable for the process of this invention, the feed must contain a contaminant, i.e. a catalytically deleterious impurity, or at least exhibit behavior consistent with such contamination. When it is not known whether or not the feed does contain such contaminant, a relatively simple test which is conducted as follows will resolve the question. About two parts of the hydrocarbon feed is mixed with one part of catalyst at room temperature, or at a higher temperature in the range of 20° F. to 212° F. if needed to make the hydrocarbon feed fluid enough for effective mixing and contact with the catalyst. The mixture is allowed to stand for about one hour, after which the treated oil is separated from the catalyst. A test is now made comparing the treated feed with the raw feed under practical catalytic conversion conditions or a realistic variant thereof, using, of course, fresh catalyst. If the rate of conversion, the temperature required for conversion, the initial equilibrium temperature, and the cycle life of the treated oil remain substantially unchanged compared with the raw oil, then the raw feed may be regarded as substantially free of contaminant and unsuitable for purposes of this invention. If, however, one or more of the recited process parameters does change, the raw feed is refinable and suitable for the present invention.

The inventors wish to emphasize that the term "contaminant," as used herein, refers to whatever substance behaves in a deleterious way in a particular catalytic conversion, and that the chemical composition of the contaminant need not be ascertained. Furthermore, the term "contaminant," or the phrase "catalytically deleterious impurity," is intended to include deleterious organic substances which occur in natural association with the hydrocarbon oil or its precursor, such as a crude petroleum, as well as materials which may be formed during processing of the feed or its precursors, such as deleterious organic substances formed in retorting shale to produce crude shale oil, or formed during hydrotreating the crude. The term also includes, of course, contaminants of well defined and known chemical structure such as furfural, sulfolane and the like which are used for extraction or separation of fractions in petroleum and petrochemicals processing. In all cases, the terms "contaminant" as used herein is to be construed in the functional sense as being catalytically deleterious for a particular catalytic conversion. Thus, a substance that is catalytically deleterious in one conversion, such as dewaxing, may also be deleterious in a different conversion such as the alkylation of benzene with ethylene, in which case that substance is a "contaminant" for both conversions; but the same substance, in the alkylation of toluene with methanol, may be benign, in which instance it is not to be regarded as a "contaminant" for present purposes. The Examiner's attention is called to, U.S. patent application Ser. No. 225,235 filed on even date herewith which describes an embodiment of this invention in which lubricating oil stocks are catalytically dewaxed, and to U.S. patent application Ser. No. 225,294 also filed on even date herewith in which an embodiment of this invention is described in which high octane gasoline is produced as a by-product.

What is claimed is:

1. A process for dewaxing a hydrocarbon oil that contains a catalytically deleterious impurity, which process comprises:

treating said hydrocarbon oil with a sorbent consisting of a first molecular sieve zeolite having pores with an effective diameter of at least about 5 Angstroms, said treatment being under sorption conditions effective to remove at least some of said impurity;

and dewaxing said treated oil by contact under dewaxing conditions with a dewaxing catalyst consisting of a second molecular sieve zeolite having pores with an effective diameter of at least about 5 Angstroms, and equal to or smaller than the effective diameter of the pores of said first molecular sieve zeolite.

2. The process described in claim 1 wherein said first molecular sieve zeolite has a Constraint Index in the range of 1 to 12 and a dried crystal density in the hydrogen form of not less than about 1.6 grams per cubic centimeter.

3. The process described in claim 2 wherein said first molecular sieve zeolite is ZSM-5 or ZSM-11.

4. The process described in claim 1 wherein said sorption conditions include a temperature of about 35° to 350° F. and a contact time effective to remove a substantial amount of said impurity.

5. The process described in claim 1 or 2 or 3 or 4 wherein said first molecular sieve zeolite and said second molecular sieve zeolite have the same crystal structure.

6. The process described in claim 1 or 2 or 3 or 4 wherein said first molecular sieve zeolite and said second molecular sieve zeolite have the same crystal structure and the same chemical composition.

7. The process described in claim 2 wherein said first and said second molecular sieve zeolites are both ZSM-5 or both ZSM-11 in a matrix, and said dewaxing is conducted in the presence of hydrogen gas at a temperature of about 500° to 800° F., at a LHSV (liquid hourly space velocity) of about 0.5 to 4.0, a pressure of about 200 to 1500 psig, and at a hydrogen to hydrocarbon mol ratio of about 2 to 10.

8. The process described in claim 1 or 2 or 3 or 4 wherein said hydrocarbon oil to be treated is derived from petroleum.

9. The process described in claim 1 or 2 or 3 or 4 or 7 wherein said hydrocarbon oil to be treated is a hydrotreated oil.

10. The process described in claim 1 or 2 or 3 or 4 or 7 wherein said hydrocarbon oil to be treated is derived from shale.

11. A method for refining a hydrocarbon feed prior to catalytic conversion at a temperature of 400°–1000° F. with a catalyst comprising a crystalline zeolite having a Constraint Index of 1 to 12, and a dried crystal density in the hydrogen form of not less than 1.6 grams per cubic centimeter, said hydrocarbon feed being selected from the group consisting of a waxy hydrocarbon oil and an aromatic hydrocarbon selected from the group consisting of benzene, toluene, xylenes, and mixtures thereof, which method comprises contacting said feed under sorption conditions including a temperature less than about 350° F. with a sorbent consisting of a crystalline zeolite having a Constraint Index of 1 to 12, and a dried crystal density in the hydrogen form of not less than 1.6 grams per cubic centimeter, and recovering a refined hydrocarbon feed.

12. The process described in claim 11 wherein each of said crystalline zeolites is selected from the group consisting of ZSM-5, ZSM-11, ZSM-12, ZSM-23, ZSM-35, ZSM-38 and ZSM-48.

13. The process described in claim 12 wherein said crystalline zeolites both are ZSM-5 or ZSM-11.

14. The process described in claim 11 or 12 or 13 wherein said hydrocarbon feed is a waxy hydrocarbon oil and said refined, recovered feed is catalytically dewaxed.

15. The process described in claim 11 or 12 or 13 wherein said hydrocarbon feed consists of a mixture of xylenes and said recovered, refined feed is isomerized.

16. The process described in claim 11 or 12 or 13 wherein said hydrocarbon feed consists of toluene and said recovered, refined feed is disproportionated.

17. The process described in claim 11 or 12 or 13 wherein said hydrocarbon feed is toluene and said recovered, refined feed is alkylated with ethylene or with methanol.

18. The process described in claim 11 wherein said contacting under sorption conditions is with a crystalline zeolite having an effective pore diameter at least as large as that of the catalyst.

* * * * *